(12) United States Patent
Mei et al.

(10) Patent No.: US 8,759,562 B2
(45) Date of Patent: Jun. 24, 2014

(54) PREPARATIVE METHOD AND APPLICATION OF ZN(II)-CURCUMIN COMPLEX AND ZN(II)-CURCUMIN SOLID DISPERSIONS

(76) Inventors: Xueting Mei, Guangzhou (CN); Donghui Xu, Guangzhou (CN); Shibo Xu, Gunagzhou (CN)

( * ) Notice: Subject to any disclaimer, the term of this patent is extended or adjusted under 35 U.S.C. 154(b) by 599 days.

(21) Appl. No.: 12/747,800

(22) PCT Filed: Jun. 4, 2008

(86) PCT No.: PCT/CN2008/001086
§ 371 (c)(1),
(2), (4) Date: Jun. 11, 2010

(87) PCT Pub. No.: WO2009/079902
PCT Pub. Date: Jul. 2, 2009

(65) Prior Publication Data
US 2010/0261923 A1    Oct. 14, 2010

(30) Foreign Application Priority Data
Dec. 14, 2007    (CN) .......................... 2007 1 0032500

(51) Int. Cl.
*C07F 3/00*    (2006.01)

(52) U.S. Cl.
USPC ........................................................ 556/400

(58) Field of Classification Search
CPC ....... C07F 3/003; C07F 51/412; C07C 45/77; C07C 49/92
USPC ........................................................ 556/131
See application file for complete search history.

(56) References Cited

U.S. PATENT DOCUMENTS

| | | | | |
|---|---|---|---|---|
| 4,263,333 | A * | 4/1981 | Maing et al. | 426/540 |
| 2008/0031980 | A1 * | 2/2008 | Rodriguez et al. | 424/773 |
| 2008/0076821 | A1 * | 3/2008 | Di Mauro | 514/475 |
| 2009/0098226 | A1 * | 4/2009 | Martelli et al. | 424/756 |

FOREIGN PATENT DOCUMENTS

| | | | |
|---|---|---|---|
| CN | 1709228 A | | 12/2005 |
| WO | WO 2007105071 A2 * | | 9/2007 |

OTHER PUBLICATIONS

Paradkar, A. et al. "Charcterization of curcumin-PVP solid dispersion obtained by spray drying," Int. J. Pharm. (2004) 271: 281-286.*
In re Wright, 999 F.2d 1557, 1561 (Fed. Cir. 1993); in re Fisher, 166 USPQ 18, 24 (CCPA 1970); *PPG v. Guardian*, 75 F.3d 1558, 1564 (Fed. Cir. 1996); in re Wands, 8 USPQ2d 1400 (CAFC 1988) at 1404; In re Angstadt, 537 F.2d 498 at 504 (CCPA 1976); Ex parte Kranz, 19 USPQ2d 1216, 1219; in re Application of Hozumi et al., 226 USPQ 353.*
Anant Paradkar et al., International Journal of Pharmaceutics 271 (2004) 281-286; abstract; Ankur Chandra, MD, Curcumin: A Review of Medical Benefits; http://www.pureprescriptions.com/expert_opinion/curcumin-turmeric.asp[Jul. 14, 2013 4:24:09 PM]).*
Wall et al. Theriogenology 69 (2008) 2-9; Lee et al. Molecular Brain 2010, 3:8 1-10 (see abstract); Goldman, LC Medicine, Saunders, 2007.; Adkinson, N. Middleton's Allergy: Principles and Practice, Elsevier, 2008.; Firestein, G. Kelley's Textbook of Rheumatology, W.B. Saunders Company, 2008.; Reviewed by Varnada Karriem-Norwood, MD on Feb. 25, 2013.*
Curcumin—NLM HSDB Database, http://toxnet.nlm.nih.gov/cgi-bin/sis/search/r?dbs+hsdb:@term+@rn+458-37-7[Jul. 15, 2013 5:32:38 PM]; Exhibit A section 2.3 Synthesis of Zn(II)-curcumin and 3.1 Characterization of the Zn(II)-curcumin complex in p. 317 and 318 of Xueting Mei et al. Chemico-Biological Interactions 181 (2009), 316-321.*
Baum, L., et al. "Curcumin interaction with copper and iron suggests one possible mechanism of action in Alzheimer's disease animal models", Journal of Alzheimer's Disease 2004, vol. 6, No. 4, pp. 367-377.
International Search Report dated Sep. 18, 2008 for PCT/CN2008/001086.

* cited by examiner

*Primary Examiner* — Fereydoun G Sajjadi
*Assistant Examiner* — Kofi Adzamli
(74) *Attorney, Agent, or Firm* — David W. Barman

(57) ABSTRACT

This invention revealed the preparative method and applications of a Zn(II)-curcumin complex and its solid dispersions. The mass ration of Zn(II)-curcumin complex and polyvinylpyrrolidone (PVP) K30 was 1:1~1:28. The Zn(II)-curcumin complex was synthesized by mixing equimolar amounts of zinc acetate and curcumin in dry ethanol and refluxing the mixture under a nitrogen atmosphere. The Zn(II)-curcumin complex precipitated, and the solid was separated by filtration and washed several times by water and ethanol to remove any unreacted curcumin and zinc acetate. Zn(II)-curcumin and PVP-k30 were added to absolute ethanol to produce a suspension by cryo-grinding under a nitrogen atmosphere. SDs of Zn(II)-curcumin/PVP were produced with a spray dryer. Zn(II)-curcumin SDs showed predominant effects in curing various senile diseases by tackling disadvantages of curcumin and surmounted the problems of monoindication and unideal therapeutic efficacy general existed in drugs for senile disease treatment. This invention is of simple preparing method and extensive application prospects.

6 Claims, No Drawings

PREPARATIVE METHOD AND APPLICATION OF ZN(II)-CURCUMIN COMPLEX AND ZN(II)-CURCUMIN SOLID DISPERSIONS

CROSS REFERENCE TO RELATED APPLICATION

This application is a National Stage of International Application No. PCT/CN2008/001086 filed Jun. 4, 2008, claiming priority based on Chinese Patent Application No. 200710032500.3, filed Dec. 14, 2007, the contents of all of which are incorporated herein by reference in their entirety.

TECHNIQUE DOMAIN

The invention involved the structure of Zn(II)-curcumin, the preparative method and medical and health-care use of Zn(II)-curcumin complex and Zn(II)-curcumin solid dispersions (SDs).

RESEARCH BACKGROUND

Curcumin (including curcumin, demethoxycurcumin, and bixdemethoxycurcumin), the main constituent of herb *Curcumia loga*, had a wide spectrum of health-care and pharmacological effects, including radical-scavenging activity, antioxidant, anti-mutagens, anti-aging, radiation protection, antivirus, anticancer, anti-hyperlipemia, anti-hypercholesterolemia, anti-atherosclerosis and antidepressant properties.

Although curcumin had a wide range of pharmacological effects, it was extremely difficult to dissolve in water, and its bioavailability was very low. It showed instability under alkaline or light conditions. All of these greatly limited its application in pharmacy fields. About 75% curcumin discharged from the feces after orally administration curcumin (1 g·kg$^{-1}$), and only trace amount of curcumin was found in urine. The intestinal absorption of curcumin was poor by determination of blood and bile excretion level of curcumin. Curcumin, dissolved with 0.5% DMSO, was used by intraperitoneal injection in animal pharmacology test. All these shows that the poor water solubility, poor oral absorption, low bioavailability limited curcumin's application in the human body. Curcumin was easily degraded in alkaline solution. The 426 nm absorption of curcumin decreased to 50% after 5 min in pH7.4 phosphate buffer solution, only 10% after 10 min later and the solution was colorless in the end. Atanu Batik reports that Cu(II)-curcumin complex has free radical scavenging poperties in vitro test. But the poor water-solubility and low bioavailability of Cu(II)-curcumin limits its application in vivo level. Search of patent, there were no medical research reports on Cu(II)-curcumin complex on pharmacy application. And there was no medical research reports on the application of water-soluble polyvinylpyrrolidone (PVP) in the preparation of Zn(II)-curcumin SDs and its medical use before this application of this patent in China.

With improvement of the living standard and medical care, the average human lifetime becomes longer and longer. Problems of the senile become more remarkable than anytime before. According to the research in Senile Institute of China, the population of the aged has rapidly increased at an average rate of 3.32% per year. Until the end of 2006, the amount of people aged over sixty in China had reached 120 million, which was equivalent to 9.5% of the total population. China has become a "senile" country due to the continuous increase of senile population. Therefore, research and development of new drugs for anti-aging and prevention of common senile diseases, had become a hot topic in medicine fields.

Zinc, as an important constituent of various enzymes in vivo, exhibits effects of promoting growth, improving gustation, accelerating wound healing, enhancing immune functions and antioxidation. Zinc deficiency induces growth retardation, malnutrition, apositia, allolriopagia and dental ulcers.

Common senile diseases includes senile dementia, fading memory, hyperlipemia, cerebral ischemia, angiosclerosis, thrombogenesis, platelet aggregation, diabetes and infectious viral diseases and so on. And in many cases one patient would appear several such diseases at the same time. However, limited by single effect on only one certain disease for most medicines, lots of cases haven't achieved satisfactory curative results yet. Therefore, the developing a new kind of new drug with favorable complex effects on multi-agedness diseases mentioned above will be very important to the health of senile people.

INVENTION CONTENTS

1. This invention aiming at the problems of monoindication and unideal therapeutic efficacy general existed in drugs for senile disease treatment, provides a noticeably therapeutical effects of Zn(II)-curcumin complex and Zn(II)-curcumin SDs with wide spectrum of application.

This invention also intends to provide preparative method of above-mentioned Zn(II)-curcumin complex and Zn(II)-curcumin SDs.

This invention further targets providing the application of above-mentioned Zn(II)-curcumin in preparing drugs or health-care products for curing diseases of hypofrontality of immune system, gastric ulcer, senile dementia, renal failure, hyperlipemia, angiosclerosis, diabetes, cerebral ischemia, degeneration of memory, myocardial ischemia, inflammation, viral infection, cancer, free radical damage, hepatic injury and depression.

To realize above-mentioned aims, the invention adopted technical schedules as follow:

In this invention, Zn(II)-curcumin complex was synthesized through two consecutive carbonyl groups of curcumin molecule along with Zinc acetate. Zn(II)-curcumin SDs were prepared by active hydrogen in curcumin molecule binding the carbonyl in PVP molecule in form of hydrogen bond with PVP-k30 as vehicle. Zn(II)-curcumin SDs greatly enhance the water-solubility of Zn(II)-curcumin complex and takes advantage of the synergistic effect between curcumin and Zinc, exhibiting stronger pharmacological effects than parent curcumin.

In Zn(II)-curcumin SDs, the mass ratio of Zn(II)-curcumin versus PVP-k30 was from 1:1 to 1:28, while optimizing ratio and best ratio were 1:3~1:18 and 1:5~1:16, respectively.

The Zn(II)-curcumin complex was synthesized by mixing zinc acetate and curcumin according to mol ratio of 1:1~1:5 in organic solvent (such as ethanol and propy alcohol) and refluxing the mixture for 3~5 h under a nitrogen atmosphere or 45~70° C. oxygen-free environment. The Zn(II)-curcumin complex precipitated, and the solid was separated by cold filtration and washed 4~6 times by 5~15° C. absolute ethanol to remove any unreacted curcumin and zinc acetate and received vacuum dehydration. Zn(II)-curcumin and PVP were proportionally added to an absolute ethanol solution to produce a suspension by cryo-grinding by high-pressure homogenizer under a nitrogen atmosphere. SDs of Zn(II)-curcumin/PVP were produced with a spray dryer.

Zn(II)-curcumin SDs could enhance the water-solubility of Zn(II)-curcumin complex with a better pharmacological effect than parent curcumin, showing a pharmacological effects in preparing drugs or health-care products for curing diseases of hypofrontality of immune system, gastric ulcer, senile dementia, renal failure, hyperlipemia, angiosclerosis, diabetes, cerebral ischemia, degeneration of memory, myocardial ischemia, inflammation, viral infection, cancer, free radical damage, hepatic injury and depression.

Zn(II)-curcumin SDs could be prepared in conventional methods with common adjuvants (eg. sodium dodecyl sulphate (SDS), cellulose microcrystallisate and magnesium stearate etc.). Zn(II)-curcumin SDs could prepare adequate dosage forms as required, such as tablet, powder, granule, capsule, slurry, syrup, ampule, transfusion or suppository. The medication is generally oral administration, and other medications such as topical administration via skin are applicable as well. The daily dose of Zn(II)-curcumin is generally 1~1000 mg with adult dose and the most common dose being 20~900 mg/d and 50~70 mg/d, respectively. The dose administration is once per day or several times per day.

Compared to existing technique, this invention possesses beneficial effects as follow:

2. Zn(II)-curcumin complex is a new complex enhancing the activity of zinc relate antioxidase in vivo with the synergic effect between curcumin and zinc, greatly improves the original pharmacological actions of curcumin.
3. Zn(II)-curcumin SDs complex increases the water-solubility of Zn(II)-curcumin complex, obviates shortcoming of curcumin's low bioavailability and poor absorption. The new invented Zn(II)-curcumin SDs shows wide spectrum of application and predominant effects in curing various senile diseases and solves the problems of monoindication and unideal therapeutic efficacy general existed in drugs for senile disease treatment.
4. This invention is of simple preparing method and extensive application prospect.

CONCRETELY ACTUALIZING EXAMPLES OF THE INVENTION

Experiment Example 1

Preparation of Zn(II)-Curcumin Complex

Curcumin, 99% pure, was manufactured by Laboratory of Traditional Chinese Medicine and Marine Drugs, School of Life Sciences, Sun Yat-sen University, China. Zinc acetate, analytical pure, was provided by Guangzhou Chemical Agent, China.

4.8 g curcumin and 2.9 g zinc acetate were dissolved in 300 ml and 150 ml absolute ethanol respectively. Zinc acetate-ethanol solvent was dropped into curcumin-ethanol solvent by stirring, and than the mixture was refluxed and heated for 3 h. The solid was separated by cold filtration after complete precipitation, and then added 300 ml 5 absolute ethanol and shook producing suspension. The suspension was centrifuged at 5000 rpm for 5 min and the sediment was collected and repeated the step of suspension and centrifugation. 4.9 g Zn(II)-curcumin complex was collected.

Experiment Example 2

The Preparation of Curcumin SDs and Zn(II)-Curcumin SDs

Curcumin, Zn(II)-curcumin complex, 99.6% pure, was provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China.

10.0 g curcumin was added to 400 ml absolute ethanol (containing 80 g PVP) to produce a suspension by cryo-grinding with high-pressure homogenizer under a nitrogen atmosphere. 86.7 g SDs of curcumin/pvp were produced with a spray dryer.

10.0 g Zn(II)-curcumin complex was added to 400 ml absolute ethanol (containing 80 g PVP) to produce a suspension by cryo-grinding with high-pressure homogenizer under a nitrogen atmosphere. 86.2 g SDs of Zn(II)-curcumin/pvp were produced with a spray dryer.

Experiment Example 3

Acute Toxicity Studies

Reagent: Zn(II)-curcumin SDs (Zn(II)-curcumin and PVP in a ratio of 1:6, w/w) was provided by provided by Laboratory of Traditional Chinese Medicine and Marine Drugs, School of Life Sciences, Sun Yat-sen University, China.

Animals: A total of 60 NIH mice weighting 18-22 g of either sex (1:1), were provided by Guangdong Medical Laboratory Animal Center, China.

Methods and Results:

A total of 20 healthy NIH mice weighting 20±2 g of either sex (1:1) were fasted for 12 h but with free access to water for 12 h. Mice of each control group received oral administration of 0.8 ml Zn(II)-curcumin SDs (200 mg/0.5 ml) solution for once, and observed for 7 successive days. Mice showed normal and agile activities with no mortality or abnormal reaction. Maximum tolerated experiment was performed under the limitation of volume of test samples.

Another 20 healthy NIH mice weighting 20±2 g of either sex (1:1) were fasted for 12 h with free access to water. Mice of each control group received 4 times oral administration of 0.5 ml Zn(II)-curcumin SDs (200 mg/0.5 ml) solution once per 3 h. Mice got free access to food and water during later 7 successive observation days. Mice showed normal activities with no mortality or abnormal reactions during observation period.

Maximum tolerated experiment was performed since mice couldn't be assayed $LD_{50}$ with the limitation of volume of test samples. The results were as follow: the maximum tolerated dose of Zn(II)-curcumin SDs was no less than 40 g·kg$^{-1}$ body weight, equivalent to no less than 5.7 g·kg$^{-1}$ body weight. During the observation period, mice showed normal activities with no mortality or abnormal reactions during observation period.

From above mentioned, it is clear that the maximum tolerated dose of Zn(II)-curcumin SDs (1:6, w/w) was no less than 40 g·kg$^{-1}$ body weight, equivalent to no less than 5.7 g·kg$^{-1}$ body weight. Zn(II)-curcumin was notoxic compounds with safe administration.

Experiment Example 4

The Protective Effects Against Myocardial Ischemia and Free Radicals

Reagents

Zn(II)-curcumin SDs (Zn(II)-curcumin and PVP in a ration of 1:6, w/w), and curcumin SDs (1:6, w/w), were prepared with the same method of mode 2, and was provided by Laboratory of Traditional Chinese Medicine and Marine Drugs, School of Life Sciences, Sun Yat-sen University, China.

China. Polyvinylpyrrolidone K30 (PVP), was subpackaging of imported adjuvants provided by Guangzhou Chemical Agent, China. The reagents were dissolved in water for oral administration when used.

SD rats were provided by Guangdong Medical Laboratory Animal Center, China. MS-302 Multimedia Biological Signal Recording and Analyzing System (Guangdong College of Life Science, China); WZ-50D micro-injection pump (Medical Instrument Factory of Zhejiang University School of Medicine, China).

Methods

SD rats received electrocardiogram (ECG) and chest lead detection, and those with abnormal offset and arrhythmia in T wave and ST segment were discarded. The qualified male and female rats weighting 210.1±20.0 g were selected and randomly divided into 3 groups (n=8): control group, curcumin group and Zn(II)-curcumin group. The control group received equal amount of PVP solution by oral administration, while other two groups received curcumin and Zn(II)-curcumin 80 mg/Kg body weight respectively by oral administration. All animals were anesthetized with ether 30 min later, recorded electrocardiogram and received hypodermic injection of isoproterenol (ISO) 2 mg/kg in rat neck. The electrocardiogram was again recorded 30 min later. At 24 h and 48 h, each group received ISO and electrocardiogram detection repeatedly as above mentioned. At 30 min after rats received oral administration of PVP, curcumin or Zn(II)-curcumin again at 72 h, blood was collected from fossa orbitalis and the serum got centrigual separation. Rats were killed and cardiac apexes were sheared and collected and prepared for 10% myocardium homogenate with 4° C. saline.

The Influence on Offset Amplitude of ΣST Segment

ST values of each rat before the first ISO administration and at 30 min after the first, second and third ISO hypodermic injection were detected. The mean value of my of ΣST was calculated as index of myocardial damage and the t-test was performed. The influences on malonaldehyde (MDA), lactate dehydrogenase (LDH) and creatinkinase (CK) in serum were detected by using kit to measure changes of MDA, LDH and CK in serum.

Results

Influence on ΣST Segment

The amplitude of ST segment basically reflects the severity of myocardial ischemia, and that is why ΣST could be regarded as the quantitative index of ischemia level. ST segment showed an evident rise after ISO hypodermic injection-induced myocardial ischemia in rats, indicating severe myocardial ischemia. As shown in Table 1, Zn(II)-curcumin SDs displayed stronger inhibiting effects on the abnormal rise of ST segment (mean amplitude of ΣST offset) than curcumin SDs.

TABLE 1

The influences on ΣST in myocardial damage mode induced by ISO in rats (x ± s, n = 8)

| Group | ΣST/mv | | |
|---|---|---|---|
| | 30 min | 24 h | 48 h |
| Control | 1.40 ± 0.28 | 1.25 ± 0.28 | 1.04 ± 0.23 |
| Zn(II)-curcumin | 0.92 ± 0.27*## | 0.81 ± 0.16**## | 0.76 ± 0.22* |
| Curcumin | 1.26 ± 0.15 | 1.05 ± 0.19 | 0.89 ± 0.20 |

Significance represented as: *$P < 0.05$, **$P < 0.01$ compared to control group; ##$P < 0.01$ compared to curcumin group.

Influences on CK, LDH and MDA in Serum

CK, LDH and MDA in serum showed evident rise after ISO hypodermic injection, indicating that damage of myocardial tissue leading to CK and LDH in myocardial cells oozing out to blood, and a significant increase of lipid per-oxidation (LPO) in serum. Results revealed that test reagents could markedly inhibit CK and LDH oozing out from myocardial cells to serum and suppress abnormal rise of MDA in serum induced by ISO in rats, exhibiting a protective effect against free radical damage.

As results showed, the protective effect of Zn(II)-curcumin SDs against ISO-induced myocardial ishchemia and free radical damage was stronger than that of curcumin SDs.

TABLE 2

Influence on serum of ISO-induced myocardial damage in rats (x ± s, n = 8)

| Group | CK (U/L) | LDH (U/L) | MDA (nmol/ml) |
|---|---|---|---|
| Control | 382.1 ± 30.7 | 337.4 ± 35.2 | 58.4 ± 5.8 |
| Zn(II)-curcumin | 289.3 ± 25.2***## | 240.6 ± 21.9***### | 28.6 ± 6.2***## |
| Curcumin | 340.5 ± 20.9** | 298.9 ± 26.4*** | 39.1 ± 5.2*** |

Significance represented as ***$P < 0.001$ compared to control group; #$P < 0.05$, ##$P < 0.01$, ###$P < 0.001$ compared to curcumin group Experiment Example 5

Protective Effects on Cerebral Ischemia and Memory Degeneration Model

Experimental Materials

Zn(II)-curcumin SDs (Zn(II)-curcumin and PVP in a ratio of 1:10(w/w)) and curcumin SDs (Curcumin and PVP in a ratio of 1:10(w/w)) were prepared by the same methods of Mode 2. They were provided by Laboratory of Traditional Chinese Medicine and Marine Drugs, Department of Biochemistry, School of Life Sciences, Sun Yat-Sen University, China. Polyvinylpyrrolidone K30 (PVP), was subpackaging of imported adjuvants provided by Guangzhou Chemical Agent, China. The reagents were dissolved in water for oral administration when used. NIH rats were provided by Guangdong Medical Laboratory Animal Center, China.

Methods and Results:

NIH mouse (18-22 g), was anaesthetized with Pentobarbital sodium (60 mg·kg$^{-1}$) prior to operation. The mice were fixed supine position, and received skin incision about 7 mm long in central neck. Both sides of common carotid artery were separated and tied up with thread (type "O"). Closed up both sides of common carotid artery for 2 min with an artery clamp in order to create cerebral ischemia, and when the cerebral ischemia ended, removed the artery clamp to let the blood flow for 5 min. Repeat the same step twice. After stopping common carotid artery blood flow, incision was stitched up, mouse was tail bleeding, and the volume of tail bleeding accounted for less than 10% of the total volume. After the operation, mouse received oral injection of physiological saline in order for blood volume supplement. In sham group, mice after being anaesthetized received separation of both sides of common carotid artery, without blood flow blocking or tail bleeding.

After both sides of common carotid artery blocked entirely, eclampsia appeared in mice first, then hypothermia and bradypnea, righting reflex disappeared in the end. Hypothermia and righting reflex fading away were the positive indexes of ischemia in experimental animals. Mice without apparently ischemic indexes were abandoned. Mice sacrificed during the ischemic process or after the operation. After restoration of blood perfusion, righting reflex recovered gradually, accelerating breathing appeared, mice returned to normal activities 3-5 h later. After operation the animals were divided into 4 groups: sham group, curcumin SDs group, Zn(II)-curcumin SDs group, control group, each group consisted of ten mice.

Mice were administered once a day, mice in control group received equal amount of PVP by oral administration. The remaining mice in each group were continuous administered 90 mg/kg curcumin or 90 mg/kg Zn(II)-curcumin respectively by oral administration for 15 d, according to Table 3. Memory test was performed after 15 d.

TABLE 3

Effects on cerebral ischemia-reperfusion brain memory injury step-through test ($\bar{x} \pm s$, n = 10)

| Group | Dose (mg · kg$^{-1}$) | Escaping latency (s) learning | memory | Numbers of errors (n) |
|---|---|---|---|---|
| Sham group | — | 37.6 ± 15.2** | 58.3 ± 20.5*** | 3.5 ± 2.0*** |
| Control group | — | 17.2 ± 10.2 | 28.5 ± 12.5 | 7.9 ± 1.6 |
| Zn(II)-curcumin group | 90 | 33.8 ± 6.2**# | 49.3 ± 14.7**# | 4.1 ± 2.3**# |
| Curcumin group | 90 | 26.3 ± 5.8 | 37.4 ± 9.4 | 6.3 ± 2.1 |

Significance represented as *P < 0.05, P < 0.01, *P < 0.001 compared with control group; #P < 0.05 compared with curcumin group.

As the result showed in Table 3, compared with control group, the response latency to enter the dark compartment of mice in sham group was obviously longer than that of mice in control group, and the number of electric shocks decreased obviously (P<0.01) These showed that cerebral ischemia-reperfusion caused a significant damage to learning and memory ability in mice. Compared with control group, Zn(II)-curcumin SDs was able to extend escaping latency significantly, and reduced the number of errors obviously. Meanwhile, Zn(II)-curcumin SDs had better protective effects on cerebral ischemia and memory degeneration than that of curcumin SDs.

Experiment Example 6

Influence on Immune Function of Organism

Materials

Zn(II)-curcumin SDs (Zn(II)-curcumin and PVP in a ratio of 1:8, w/w), and curcumin SDs (1:8, w/w), were prepared with the same method of Mode 2, and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used. NIH mice and SD rats were provided by Guangdong Medical Laboratory Animal Center, China. Gallus domesticas were bought from food market of Sun Yat-sen University, China.

Experiment Method

Influence on the Thymus and Spleen of Mice

A total of 40 healthy NIH mice weighting 18~22 g of either sex (1:1) were used in this study. 10 mice of either sex (1:1) were randomly chose as normal group, and other 30 mice received peritoneal injection of cyclophosphamide 60 mg/Kg body weight and were randomly divided into 3 groups (n=10, male: female=1:1): control group, curcumin group and Zn(II)-curcumin group. Test reagents were given in way of oral administration. Normal group and control group received equal amount of PVP, while curcumin group and Zn(II)-curcumin group received test reagents equivalent to curcumin or Zn(II)-curcumin 50 mg/Kg body weight respectively. All animals received test reagent for 30 successive days, and in the 30$^{th}$ day mice of each group were fasted for one day but with free access to water. In the 31$^{st}$ day, mice of each group were sacrificed, and their body weight, the weight of thymus and spleen were weighed. Indexes of thymus and spleen were calculated and the group differences were compared.

Experimental Results

TABLE 4

Effects on thymus and spleen in mice ($\bar{x} \pm SD$, n = 10)

| Group | Dose (mg/kg) | Thymus Index (mg/10 g body weight) | Spleen Index (mg/10 g body weight) |
|---|---|---|---|
| Control group | — | 13.21 ± 4.35 | 47.24 ± 8.35 |
| Normal group | — | 28.14 ± 5.65*** | 75.31 ± 12.25*** |
| Zn(II)-curcumin group | 50 | 22.84 ± 5.37***# | 61.24 ± 15.24***# |
| Curcumin group | 50 | 17.62 ± 4.52 | 48.27 ± 11.34** |

Significance represented as P < 0.01, *P < 0.001 compared to control group; #P < 0.05 compared to curcumin group.

Compared to control group, Zn(II)-curcumin and curcumin could significantly increased indexes of thymus and spleen in mice, exhibiting effect of improving immune functions. Meanwhile, Zn(II)-curcumin SDs had better effects on improving immune functions than curcumin SDs (p<0.05).

Experiment Example 7

Effects Against Kidney Failure

Materials

NIH mice (18-22 g) of either sex (1:1), were provided by Guangdong Medical Laboratory Animal Center, China.

Zn(II)-curcumin SDs (Zn(II)-curcumin and PVP in a ratio of 1:8, w/w), curcumin SDs (1:8, w/w) were prepared by the same methods of Mode 2. They were provided by Laboratory of Traditional Chinese Medicine and Marine Drugs, Department of Biochemistry, School of Life Sciences, Sun Yat-Sen University, China. Polyvinylpyrrolidone K30 (PVP), was subpackaging of imported adjuvants provided by Guangzhou Chemical Agent, China. The reagents were dissolved in water for oral administration when used.

Experiment Methods

Endotoxin-Induced Acute Renal Failure Model

Forty mice were divided into four groups randomly (each of them consisted of 10 mice), including normal group, control group, curcumin group, Zn(II)-curcumin group. Test reagents were given in way of oral administration. Normal group and control group received equal amount of PVP, while curcumin group and Zn(II)-curcumin group received test reagents equivalent to curcumin or Zn(II)-curcumin 50 mg/Kg body weight respectively. And mice in normal group received equal amount of PVP injection in caudal vein, then other mice received endotoxin injection (0.06 g/kg) in caudal vein. After 5 hours, specimen of blood of mice was collected, the levels of blood urea nitrogen (BUN) and creatinine (Cr) were determined. Selected a kidney from mouse in each mice and made it into homogenate 100 ml·L$^{-1}$ respectively, then determined the activity of Glutathione peroxidase (GSH-Px).

Experimental Result

Compared with control group, Zn(II)-curcumin SDs effectively inhibited increasement of BUN and Cr by induced by endotoxin, increased the enzyme activity of GSH-Px, and showed better protective effect on endotoxin-induced acute renal failure than curcumin SDs ($p<0.01$).

18-22 g of either sex (1:1) were provided by Guangdong Medical Laboratory Animal Center, China.

Reagents for senile dementia induction: Amyloid β-protein (Aβ 1-42 fragment), molecular mass 4514.1 (Sigma Chemical Co., product NO. 107761-42-2).

Methods and Results

A total of 40 NIH mice of either sex (1:1) were randomly divided into 4 groups (n=10 per group): normal group, control group, curcumin group, Zn(II)-curcumin group. Normal group and control group received equal amount of PVP by oral administration, while curcumin group and Zn(II)-curcumin group received test reagents equivalent to curcumin or Zn(II)-curcumin 50 mg/Kg body weight by oral administration respectively. Mice of each group (except normal group) were anesthetized with 0.54% pentobarbital sodium 0.1 ml/10 g body weight by peritoneal injection. After disinfected by iodine tincture and alcohol, skin of vertex cranial were disclosed along the middle of lengthwise and cranial bones were exposed. Pinholes (2.0 mm lower than bregzna point at both sides, 2.5 mm to the middle) were pierced by injector and slowly injected 2 μl Aβ solution (density: 7 μg/μl) by 5 μl injector in 30 min. Injectors were dislodged after retained for 5 min and the skin was sewed up. Mice was administered test reagents the day after modeling for 30 successive days and received oral administration once per day.

Step Down Test:

Training began at the day after drug administration: animals were placed in test chamber with copper grid floor to adapt the environment for 3 min. Then the 36v electric current

TABLE 5

Effect of tested compound on acute renal failure ($\bar{x} \pm SD$, n = 10)

| Group | Dose mg/kg | Cr/10 mg·L$^{-1}$ | BUN/10 mg·L$^{-1}$ | GSH-Px/nU·L$^{-1}$ |
|---|---|---|---|---|
| Normal group | — | 17.5 ± 2.4*** | 247.5 ± 23.2*** | 50.2 ± 22.4*** |
| Control group | — | 70.2 ± 20.1 | 420.3 ± 27.8 | 28.7 ± 10.6 |
| Zn(II)-curcumin group | 50 | 35.3 ± 11.4**## | 283.0 ± 25.4***### | 34.5 ± 9.2**## |
| Curcumin group | 50 | 48.2 ± 7.2*** | 362.4 ± 31.7*** | 22.4 ± 5.9* |

Significance represented as P<0.01, *P<0.001 compared with control group; ##P<0.01 compared with Curcumin group.

Experiment Example 8

Pharmacological Effects Against Senile Dementia

Reagents

Zn(II)-curcumin SDs (Zn(II)-curcumin and PVP in a ratio of 1:8, w/w), and curcumin SDs (1:8, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used. A total of 60 NIH mice weighting was delivered through the copper grid floor. Once mice stood on the grid floor, a scrambled foot shock was delivered through the grid floor. Mice could escape from the shock only by jump onto the insulated platform in the chamber to avoid nociceptive stimuli. Most animals might jump to the grid floor again or for several times and jump back to the platform on getting electric shock. The training process lasted for 5 min (the training time for all mice was the same in the same test) and the number of errors (jump down the platform) was measured. Twenty-four hours after the training, mice were again placed in the reaction chamber for memory retention test. The response latency to jump down the platform, the total number of errors (jump down the platform) in 3 min and the frequency of wrong behaviors were measured.

TABLE 6

Effects on step down test of Aβ-induced dementia rat model
($\bar{x} \pm SD, n = 10$)

| Groups | Dose (mg/kg) | Number of electric shock in 5 min (n) | 24 h later Response laterncy(s) | Frequency of error in 3 min |
|---|---|---|---|---|
| Control | — | 4.1 ± 1.7 | 81.5 ± 16.7 | 4.1 ± 1.2 |
| Zn(II)-curcumin | 50 | 1.5 ± 1.2***# | 117.4 ± 21.4***# | 1.9 ± 0.8*** |
| Curcumin | 50 | 2.8 ± 1.4 | 95.8 ± 11.5 | 2.5 ± 1.2* |
| Normal | — | 1.4 ± 1.0***# | 120.6 ± 24.7***# | 1.5 ± 0.7***# |

Significance represented as *P < 0.05, P < 0.01, *P < 0.001 compared to control group; #P < 0.05 compared to curcumin group.

Senile dementia was characterized by neurocyte death, neurofibrillary tangles and senile plaques' appearance in neurocyte and blood vessels in cerebrum. The dementia model was formed by Aβ protein injection into hippocampus of mice leading to senile plaques' appearance in neurocyte and blood vessels in cerebrum. Zn(II)-curcumin SDs evidently strengthened the memory acquirement and strengthen of mice of senile dementia model, indicating its stronger effects against senile dementia than curcumin SDs (p<0.05).

Experiment Example 9

Pharmacological Effects on Arteriosclerosis

Experimental Materials

Zn(II)-curcumin SDs (Zn(II)-curcumin and PVP in a ratio of 1:8, w/w), curcumin SDs (curcumin and PVP in a ratio of 1:8, w/w) were prepared by the same methods of Mode 2. They were provided by Laboratory of Traditional Chinese Medicine and Marine Drugs, School of Life Sciences, Sun Yat-Sen University, China. Polyvinylpyrrolidone K30 (PVP), was subpackaging of imported adjuvants provided by Guangzhou Chemical Agent, China. The reagents were dissolved in water for oral administration when used. Male SD rats were provided by Guangdong Medical Laboratory Animal Center, China.

Experimental Methods

Thirty healthy SD male rats (275±20 g) were divided into three groups randomly (n=10 per group): control group, curcumin group, Zn(II)-curcumin group. Control group received equal amount of PVP by oral administration, while curcumin group and Zn(II)-curcumin group received SDs containing curcumin or Zn(II)-curcumin 80 mg/Kg body weight by oral administration respectively. Rats were continuously administered tested samples for 15 d according to Tab.9. Rats were fasted for 12 h on the 16th day. 1 h after receiving tested samples, rats were anesthetized by lumbar injection of 4% amobarbital sodium (42 mg/kg), then were fixed on operation table in supine position and received carotid artery-carotid vein intubatton. Air pipe of rat was separated and then a short plastic pipe was inserted in order to aspirate tracheal secretions. Left common carotid artery and right vena jugularis externa were separated. A polyethylene plastic soft tube (7.3 cm long, 0.15 cm inner diameter, 0.03 cm thick) was threaded with a medical suture (8 cm long) and was injected with lipo-hepinette solution (50 U/ml). One end of the polyethylene plastic tube was inserted into right vena jugularis externa, while the other end inserted into left common carotid artery. Ligation was performed in order to fix the tube. Then blood flow was flow from left common carotid artery to right vena jugularis externa through the polyethylene plastic tube. Blood flow was maintained for 15 min exactly, and then interruption was given immediately. The medical suture was taken out and its total wet weight was weighed by electronic analytical balance. The wet weight of thrombus was equal to the total wet weight minus the dry weight of medical suture.

Thirty healthy SD male rats (275±20 g) were divided into three groups randomly (n=10 per group): control group, curcumin group, Zn(II)-curcumin group. Control group received equal amount of PVP by oral administration, while curcumin group and Zn(II)-curcumin group received SDs containing curcumin or Zn(II)-curcumin 80 mg/Kg body weight by oral administration respectively. Rats were continuously administered tested samples for 15 d according to Tab.9. Rats were fasted for 12 h on the 16th day. 0.5 h after receiving tested samples, rat was anesthetized by lumbar injection of mebumal sodium (30 mg/kg). Common carotid artery was separated, blood was collected by polyethylene plastic tube with 3.8% sodium citrate as anticoagulant (anticoagulant and blood in a ratio of 1:9, V/V), and then received centrifugation 800 rmp for 5 min. Upper layer of platelet-rich plasma (PRP) was imbibed, and the remaining part received centrifugation 3000 rpm for 10 min. Then the upper layer of remaining part was platelet poor plasma (PPP), which was mixed with PRP to keep level of blood platelet up to 0.6~0.9 million/mm$^3$.

In order to eliminate the influence of different platelet count according to nephelometry, PRP and PPP from the same blood sample were used as the zero point and top point respectively. PRP was defined as a coordinates point as 0%, and PPP was defined as a coordinates point as 100%. Every tube was added 20 μl PRP and platelet aggregation was induced by 20 μl inducer (4 mm AA or 3.0 μm ADP prepared by 0.2 m/l pH7.4 phosphate buffer). Platelet aggregation was determined within 10 min.

TABLE 7

Inhibited effect on thrombosis in rats ($\bar{x} \pm SD, n = 10$)

| | | Item | |
|---|---|---|---|
| Group | Dose (mg/kg) | Wet weight of thrombus (mg) | Inhibition rate of thrombus (%) |
| Normal Group | — | 102.4 ± 12.5 | — |
| Zn(II)-curcumin Group | 80 | 58.7 ± 7.9***### | 42.7 |
| Curcumin Group | 80 | 80.4 ± 8.5*** | 21.5 |

Significance represented as ***p < 0.001 compared with normal group; ###P < 0.001 compared with curcumin group.

TABLE 8

Effect on platelet aggregation rate in rats ($\bar{x} \pm SD$, n = 10)

| Group | Dose mg/kg | AA-induced platelet aggregation rate (%) | ADP-induced platelet aggregation rate (%) |
|---|---|---|---|
| Normal Group | — | 85.4 ± 6.3 | 82.5 ± 8.3 |
| Zn(II)-curcumin Group | 80 | 49.8 ± 7.6***### | 46.1 ± 7.2***## |
| Curcumin Group | 80 | 60.5 ± 6.7*** | 62.8 ± 8.3*** |

Significance represented as ***p < 0.001 compared with normal group; ##P < 0.01, ###P < 0.001 compared with curcumin group.

According to the results of thrombosis and platelet aggregation in rats, Zn(II)-curcumin SDs exhibited evident anti-thrombotic effect and anti-platelet aggregation. It indicated that Zn(II)-curcumin SDs had stronger anti-atherosclerosis effect than curcumin SDs (p<0.01).

Experiment Example 10

Pharmacological Effects on Disturbance of Lipid Metabolism Model

Reagents

Zn(II)-curcumin SDs (Zn(II)-curcumin and PVP in a ratio of 1:8, w/w), and curcumin SDs (1:8, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used.

Animals

Male SD rats were provided by Guangdong Medical Laboratory Animal Center, China.

Experimental Methods

Healthy male SD rats (200±20 g) were fed with normal diet in laboratory environment and observed for 6 consecutive days. No abnormality was observed. Blood was collected by tail cut, serum was separated, and blood fat indexes were determined. Fifty rats with normal blood fat indexes were chose for this study with free access to food and water. Those rats were oral administered with high-fat food (80% axungia porci+4% sodium cholate+4% cholesterin+12% egg yolk powder) 20 ml/kg at a set time in the morning for 30 consecutive days. All rats were fasted for 12 h in the $31^{st}$ day. Blood was collected by tail cut, serum was separated and the contents of triglyceride (TG), total cholesterol (TC) were tested. Thirty rats whose TC content was higher than 600 mg/dl were selected and randomly divided into 3 groups (n=10): control group, curcumin group and Zn(II)-curcumin group. Rats of control group received equal amount of PVP solution, while rats of curcumin group and Zn(II)-curcumin group received SDs containing curcumin or Zn(II)-curcumin 50 mg/kg body weight. Rats received test reagents for 25 successive days, and were fasted for 12 h at $26^{th}$ day, and their blood was collected for blood fat indexes were tested.

TABLE 9

The effects on disturbance of lipid metabolism model in rats ($\bar{x} \pm SD$, n = 10)

| Group | Dose mg/Kg | Triglyceride (TG) (mg/dl) | Total cholesterol(TC) (mg/dl) | High density lipoprotein cholesterol (HDL-C) (mg/dl) |
|---|---|---|---|---|
| Control | — | 166.3 ± 24.5 | 845.7 ± 80.6 | 30.4 ± 8.2 |
| Zn(II)-curcumin | 50 | 83.4 ± 12.7***### | 384.2 ± 57.2***### | 72.3 ± 7.4***## |
| Curcumin | 50 | 134.2 ± 19.1** | 542.7 ± 68.9*** | 59.2 ± 6.3** |

Significance represented by p < 0.01, *p < 0.001 compared to control group; ##P < 0.01, ###P < 0.001 compared to curcumin group.

Results indicated that Zn(II)-curcumin SDs displayed evident therapeutic effect against hyperlipemia and hypercholesterolemia, which was better than curcumin SDs (p<0.01).

Experiment Example 11

Pharmacological Effect on Diabetes Model

Reagents

Zn(II)-curcumin SDs (Zn(II)-curcumin and PVP in a ratio of 1:8, w/w), curcumin SDs (curcumin and PVP in a ratio of 1:8, w/w) were prepared by the same methods of Mode 2. They were provided by Laboratory of Traditional Chinese Medicine and Marine Drugs, Department of Biochemistry, School of Life Sciences, Sun Yat-Sen University, China. Polyvinylpyrrolidone K30 (PVP), was subpackaging of imported adjuvants provided by Guangzhou Chemical Agent, China. The reagents were dissolved in water for oral administration when used. Alloxan, produced by Sigma Chemical Co.

Animals

NIH rats were provided by Guangdong Medical Laboratory Animal Center, China.

Methods and Results

Ten mice were selected randomly from 50 healthy male NIH mice (18~22 g) as normal group. The remaining mice were fasted for 12 h, then received intraperitoneal injection of Alloxan 250 mg/kg weight, and were oral administered glucose solution 2.5 g/kg 6 h later in order to make the mice get through hypoglycemia period. Mice got access to food and water, and were fasted again for 12 h after 36 h. Blood was collected from orbital vein in mice, and glucose level of mice which received intraperitoneal injection of Alloxan was tested. Thirty mice of which glucose level higher than 200 mg/dl were selected and divided into three groups randomly. They were hyperglycemia group, curcumin SDs group, Zn(II)-curcumin SDs group, and every of them consisted of 10 mice. Mice in normal group and hyperglycemia group were administered equal amount of PVP solution respectively by oral administration. Mice in curcumin SDs group and Zn(II)-curcumin SDs group were oral administered SDs containing curcumin or Zn(II)-curcumin 40 mg/kg weight respectively. Mice were continuously administered tested samples for 12 d and were fasted for 12 h before the last administration. Blood was collected from orbital vein in mice 1 h after mice received tested samples and blood-sugar content was determined by glucose test kits.

TABLE 10

Pharmacological effect on Alloxan-induced diabetes mellitus model ($\bar{x} \pm SD$, n = 10)

| Group | Dose (mg/Kg weight) | Glucose values (mM/L) | Hypoglycemic rate (%) |
|---|---|---|---|
| Normal group | — | 6.41 ± 1.20*** | — |
| Hyperglycemia group | — | 29.31 ± 5.41 | — |
| Zn(II)-curcumin Group | 40 | 21.45 ± 1.37***### | 26.8 |
| Curcumin Group | 40 | 25.48 ± 1.36* | 13.6 |

Significance represented as p<0.01, *p<0.001 compared with Hyperglycemia Group; ##P<0.01 compared with Curcumin Group.

Compared with hyperglycemia group, Zn(II)-curcumin SDs showed evident effect of reducing high glucose concentration in Alloxan-induced diabetes model (p<0.001). Zn(II)-curcumin SDs had a better effect of reducing high glucose concentration than curcumin SDs (p<0.001).

Experiment Example 12

Pharmacological Effects Against Hepatitis B Virus

Experimental Samples

Zn(II)-curcumin SDs (Zn(II)-curcumin and PVP in a ratio of 1:8, w/w), and curcumin SDs (curcumin and PVP in a ratio of 1:8, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used.

Animals

New Zealand rabbits provided by Laboratory Animal Center of School of Medicine, Sun Yat-sen University, were with free access to water and ordinary rabbit feed.

Reagents

HBsAg, was provided by National Institute of Pharmaceutical and Biological Products. HBeAg ELISA kit was produced by Shanghai Kehua Bio-Tech. Co., Ltd. HbsAg positive serum was provided by clinical laboratory of the First Affiliated Hospital of Guangzhou University of Chinese Medicine, which was the mixture of 20 samples of HBsAg positive serum (HBsAg, HBeAg, anti-HBc, HBV DNA were positive) and was preserved in −20° C. refrigerator.

Methods and Results

Medicated serum was prepared as follow: twenty-four New Zealand rabbits (2.0±0.2 kg) was selected and randomly divided into control group, curcumin group and Zn(II)-curcumin group. Each group was consisted of eight rabbits of either sex (1:1). Rabbits of control group oral administered equal amount of PVP solution, while rabbits of curcumin group and Zn(II)-curcumin group oral administered SDs containing curcumin or Zn(II)-curcumin 200 mg/Kg body weight respectively. Rabbits were administered once per day for 8 consecutive days. One hour after the last administration, blood was collected from heart, and serum was sterilely separated. Some part of serum was inactivated at 56° C. for 30 min while the other was activated. Both inactivated serum and activated serum received filtration sterilization by 0.45 μm milipore filter respectively and were preserved in −20° C. refrigerator.

The content of HBsAg in HBsAg positive serum was determined. HBsAg positive serum was diluted with saline containing 20% calf serum in ratio of 1:2, 1:4, 1:8, 1:16, to 1:16384. The P/N values of samples and 1 μg/L, 2 μg/L, 5 μg/L HBsAg standard were tested by ELISA. Detections were repeated for 3 times with duplicated parallel experiment for each time. The level of HBsAg in HBsAg positive serum was determined according to the standard curve of HBsAg density—P/N value, and the serum was preserved in −20° C. refrigerator.

The influence of blank serum inactivation on HBeAg: 200 μl inactivated rabbit serum, 200 μl activated rabbit serum and 200 μl saline containing 20% calf serum were respectively interacted with 50 μl 500 μg/L HBsAg positive serum at 37° C. for 4 h. Ten holes of parallel experiment were made for each sample. The P/N value of HBeAg after interaction was determined by HBeAg ELISA test kit and t-test analysis was performed.

Medicated serum (200 μl) and blank rabbit serum (200 μl) were respectively interacted with 50 μl HBsAg positive serum (500 μg/L) at 37° C. for 4 h. Ten holes were made for each sample. The P/N value of HBeAg after interaction was determined by HBeAg ELISA diagnostic kit and t-test Analysis was performed.

The effects of inactivated blank rabbit serum HbeAg: Inactivated blank rabbit serum and activated bland rabbit serum were respectively interacted with 500 μg/L HBsAg positive serum at 37° C. for 4 h. The P/N value of HBeAg after interaction was determined. The result indicated that activated blank serum could inhibit activities of HBeAg. There was a markedly difference between the influences of unactivated serum and activated serum on HBeAg (P<0.05). Thus rabbits' blank serum and medicated serum were inactivated at 56° C. for 30 min in following experiment.

TABLE 11

Influence of blank serum inactivation on HBsAg ($\bar{x} \pm SD$)

| Group | Hole number | P/N value |
|---|---|---|
| Saline containing 20% calf serum | 10 | 5.02 ± 0.54 |
| Inactivated blank rabbit serum | 10 | 4.96 ± 0.41Δ |
| activated blank rabbit serum | 10 | 4.27 ± 0.39** |

Significance represented as ΔP<0.05 compared to saline with 20% calf serum; ***P<0.001 compared to inactivated blank rabbit serum.

TABLE 12

Inhibition of medicated serum on HBeAg ($\bar{x} \pm SD$)

| Group | Hole number | P/N value |
|---|---|---|
| Inactivated blank rabbit serum | 10 | 5.82 ± 0.44 |
| Zn(II)-curcumin | 10 | 3.57 ± 0.43***### |
| Curcumin | 10 | 4.56 ± 0.41*** |

Significance represented as ΔP > 0.05, ***P < 0.001 compared to inactivated blank rabbit serum; #P < 0.05, ##P < 0.01, ###P < 0.001 compared to curcumin group.

Compared with inactivated blank serum, Zn(II)-curcumin SDs showed evident inhibition on hepatitis B virus (p<0.001). Zn(II)-curcumin SDs also showed evident inhibition on hepatitis B virus than curcumin SDs (p<0.001).

Experiment Example 13

Effect on Ethanoic Acid-Induced Gastric Ulcer Model in Rats

Reagents

Zn(II)-curcumin SDs (Zn(II)-curcumin and PVP in a ratio of 1:8, w/w), curcumin SDs (curcumin and PVP in a ratio of 1:8, w/w) were prepared by the same methods of Mode 2. They were provided by Laboratory of Traditional Chinese Medicine and Marine Drugs, Department of Biochemistry, School of Life Sciences, Sun Yat-Sen University, China. Polyvinylpyrrolidone K30 (PVP), was subpackaging of imported adjuvants provided by Guangzhou Chemical Agent, China. The reagents were dissolved in water for oral administration when used.

Animals

Male SD rats were provided by Guangdong Medical Laboratory Animal Center, China.

Thirty healthy SD rats (200±10 g) of either sex (1:1) were selected. Rats were fasted 24 h but had free access to water before experiment and were anaesthetized with 30 mg/kg mebumal sodium. Rats underwent a laparotomy at the point of 2 cm lower than the xiphoid process in aseptic condition. 0.02 ml of acetic acid was poured through on the surface of gastric serosa via a glass tube (5 mm internal diameter, 30 mm long). Acetic acid was aspirated by cotton bud 1 min later. Gastric serosa was then washed twice with physiological saline and incision was sewed up. Rats were divided into three groups randomly. Each group consisted of 10 rats of either sex (1:1). Rats in normal group were administered PVP solution 500 mg/kg weight (excluding the influence of adjuvant on gastric mucosa). Rats in curcumin SDs group and Zn(II)-curcumin SDs group were administered relevant SDs containing curcumin or Zn(II)-curcumin 200 mg/kg weight respectively. Rats were administered for 14 consecutive days, and were fasted 24 h but had free access to water on the 15$^{th}$ day. Then 3 ml of blood was collected from orbital vein and 2 ml of it was injected into a test-tube filled with trasylol and 304 of 10% EDTA-Na$_2$, and then mix them together completely. The homogenate received centrifugation at 3000 rmp for 10 min at 4, and then plasma was separated and received preservation at −20. The remaining 1 ml of blood was injected into glass tube and separated serum after kept for a while at room temperature, and preserved at −20. The test of serum NO and plasma ET were performed according to the kit specification.

Rats were sacrificed by dislocation of cervical vertebra, and their abdomens were incised and pyloric ligation was performed. Then their stomach was removed and fixed by injecting 5 ml of 4% formaldehyde solution. Thirty minutes later, each stomach was opened along the greater curvature and turned inside out to clean the food debris. The shape of ulcer presented circular shape or elliptical shape. The longest diameter and the shortest diameter of ulcer area were measured and ulcer index was determined by the average value of them. Statistical comparison was performed among every group, ulcer suppression ratio was calculated according to formula 1-1.

Ulcer healing percentage(%)=(Ulcer diameter mean in control group−Ulcer diameter mean in experimental group)/Ulcer diameter mean in control group×100%  1-1

Compared with control group, Zn(II)-curcumin SDs showed evident effects on anti-gastric ulcer (p<0.001). Compared with curcumin SDs group, Zn(II)-curcumin SDs showed evident effects on anti-gastric ulcer (p<0.001).

TABLE 13

Effect on acid-induced gastric ulcer ($\bar{x} \pm SD$, n = 10)

| Group | Dose (mg/kg) | Ulcer index | Healing ratio (%) |
|---|---|---|---|
| Control Group (treated with PVP) | 500 | 9.76 ± 0.69 | — |
| Zn(II)-curcumin Group | 50 | 3.72 ± 0.35***### | 61.9 |
| Curcumin Group | 50 | 5.26 ± 0.10*** | 46.1 |

Significance represented as ***p < 0.001 compared with control group; ###P < 0.001 compared with curcumin group.

Effect on Serum NO and Plasma et Contents

Compared with control group, Zn(II)-curcumin SDs increased serum NO level and decreased plasma ET level (p<0.001). Zn(II)-curcumin SDs increased serum NO level and decreased plasma ET level than curcumin SDs (p<0.001).

TABLE 14

Effect on serum NO and plasma ET contents ($\bar{x} \pm SD$, n = 10)

| Group | Dose (mg/kg) | Serum NO (μmol/mL) | Plasma ET (pg/mL) |
|---|---|---|---|
| Control Group (treated with PVP) | 500 | 31.4 ± 6.5 | 213.1 ± 25.3 |
| Zn(II)-curcumin group | 50 | 52.5 ± 11.4***# | 125.7 ± 14.2***### |
| Curcumin group | 50 | 40.4 ± 7.6* | 156.7 ± 20.9*** |

Significance represented as ***p < 0.001 compared with normal group; #P < 0.05, ##P < 0.01 compared with curcumin group.

Experiment Example 14

Anti-Inflammatory Experiment on Tampon-Induced Granuloma in Rats

Reagents

Zn(II)-curcumin SDs (Zn(II)-curcumin and PVP in a ratio of 1:8, w/w), and curcumin SDs (1:8, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used.

Animals

Male SD rats were provided by Guangdong Medical Laboratory Animal Center, China.

Experiment of Tampon-Induced Granuloma in Rats

A total of 30 healthy male SD rats (180-200 g) were divided into 3 groups (n=10), namely control group, curcumin group and Zn(II)-curcumin group. Rats were lightly anesthetized with ether and unhairing abdomens were sterilized with 75% alcohol and iodine tincture. An incision was made in the abdomen center and two sterile tampons (each tampon weighting 29 mg, sterilized with auto-claving, was added alpen 1 mg/0.1 ml, and was dried in oven at 50° C.) were subcutaneously embed into arm pits (or groin) at both side of rats. The incision was sterilized with 75% alcohol and iodine tincture after saturation. The day performed operation began oral administration. Rats of control group received equal amount of PVP solution, while curcumin group and Zn(II)-curcumin group received SDs containing curcumin or Zn(II)-curcumin 60 mg/Kg body weight. The administration was once per day for 14 consecutive days. In the $15^{th}$ day, rats sacrificed by cervical dislocation, and tampon granuloma tissues were exposed and taken out and dried in oven at 60° C. for 12 h. The dry weights were weighed. Experimental results received statistical treatment and group differences were compared.

Rats showed fine healing after tampon embedment. After 14-day administration, granuloma in armpits of rats of control group grew obviously. Compared with control group, Zn(II)-curcumin SDs markedly inhibited the hyperplasia of tampon granuloma having anti-inflammation effects (p<0.001). Zn(II)-curcumin SDs showed stronger anti-inflammation effects than curcumin SDs (p<0.001).

TABLE 15

Influence on tampon-induced granuloma in rats

| Group | Dose (mg·Kg$^{-1}$) | Weight of granuloma (mg) | Inhibition rate (%) |
|---|---|---|---|
| Control group | — | 125.4 ± 29.5 | — |
| Zn(II)-curcumin group | 50 | 66.8 ± 7.2***### | 46.7 |
| Curcumin group | 50 | 85.4 ± 9.6*** | 31.9 |

Significance represented as ***P < 0.001 compared to control group; ###P < 0.001 compared to curcumin group.

Experiment Example 15

Anti-Tumor Experiment

Reagents

Zn(II)-curcumin SDs (Zn(II)-curcumin and PVP in a ratio of 1:8, w/w), and curcumin SDs (1:8, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used.

Animals and Cells

NIH mice were provide by Guangdong Medical Laboratory Center, China.

Ehrlich ascites tumor cells, transplanted sarcoma cells (S180) and transplanted hepatoma cells (HepA) were provided by Sun Yat-sen University Cancer Center, China.

Effects on Transplanted Sarcoma in Mice

Thirty mice received hypodermic inoculation of 0.2 ml sarcoma S180 cell suspension ($1.0 \times 10^7$/L) at right armpit and at the next day after inoculation randomly divided into 3 groups (n=10): control group, curcumin group and Zn(II)-curcumin group. Mice of control group received equal amount of PVP by oral administration, while mice of curcumin and Zn(II)-curcumin group received SDs containing curcumin or Zn(II)-curcumin 60 mg/Kg body weight. Mice were administered once per day for 10 consecutive days. All animals were sacrificed at the $11^{th}$ day. The weight of body, thymus and spleen were measured and tumor inhibition rate was calculated according to the following formula:

Inhibition Rate(%)=(1−Mean Tumor Weight of medicated group/Mean Tumor Weight of control group)×100%

Influence on Life Span of HepA Mice

Thirty mice received intraperitoneal inoculation of 0.2 ml HepA cell suspension ($1.0 \times 10^7$/ml) and at the next day were randomly divided into 3 groups (n=10), namely control group, curcumin group and Zn(II)-curcumin group. Mice of control group received equal amount of PVP solution, while mice of curcumin and Zn(II)-curcumin group received SDs containing curcumin or Zn(II)-curcumin 60 mg/Kg body weight. Mice were administered once per day for 10 consecutive days. Days before a mouse's natural death were recorded and the increase life span was calculated according to following formula:

Increase Life Span=(Mean Survival Days of experimental group/Mean Survival Days of control group−1)×100%

Influence on Ehrlich Ascites Tumor in Mice

Thirty mice received intraperitoneal inoculation of 0.2 ml Ehrlich ascites tumor ($1.0 \times 10^7$/ml) and at the next day were randomly divided into 3 groups (n=10), namely control group, curcumin group and Zn(II)-curcumin group. Mice of control group received equal amount of PVP solution, while mice of curcumin and Zn(II)-curcumin group received SDs containing curcumin or Zn(II)-curcumin 60 mg/Kg body weight. Mice were administered once per day for 10 consecutive days. Days before a mouse's natural death were recorded and the increase life span was calculated according to following formula:

Increase Life Span=(Mean Survival Days of experimental group/Mean Survival Days of control group−1)×100%

Inhibition Rate(%)=(1−Mean Tumor Weight of medicated group/Mean Tumor Weight of control group)×100%

TAB. 16

Inhibition of transplanted sarcoma S180 of mice($\bar{x} \pm s$, n = 10)

| Group | Dose mg/Kg | Tumor Weight (g) | Inhibition Rate (%) | Thymus Index (mg/10 g body weight) | Spleen Index (mg/10 g body weight) |
|---|---|---|---|---|---|
| Control group | — | 1.50 ± 0.46 | — | 21.7 ± 3.4 | 72.5 ± 8.2 |
| Zn(II)-curcumin group | 60 | 0.62 ± 0.32***## | 52.0 | 30.2 ± 5.72***### | 89.6 ± 9.4** |
| Curcumin group | 60 | 0.84 ± 0.40** | 44.0 | 25.5 ± 3.4** | 76.4 ± 5.9** |

Significance represented as
$P < 0.01$, *$P < 0.001$ compared to control group;
$P < 0.01$, ###$P < 0.001$ compared to curcumin group.

TABLE 17

Influence on the life span of HepA mice ($\bar{x} \pm s$, n = 10)

| Group | Dose/ mg/Kg | Life Span (day) | Increase Life Span (%) |
|---|---|---|---|
| Control | — | 13.5 ± 2.7 | — |
| Zn(II)-curcumin | 60 | 20.5 ± 8.5***### | 34.1 |
| Curcumin | 60 | 16.2 ± 3.8 | 20.0 |

Significance represented as *$p < 0.05$, $P < 0.01$, *$P < 0.001$ compared to control group; ###$P < 0.001$ compared to curcumin group.

TABLE 18

Influence on the life span of mice with Ehrlich ascites tumor ($\bar{x} \pm s$, n = 10)

| Group | Dose (mg/Kg) | Life Span (day) | Increase Life Span (%) |
|---|---|---|---|
| Control group | — | 14.2 ± 2.5 | — |
| Zn(II)-curcumin group | 60 | 19.4 ± 5.2*## | 36.6 |
| Curcumin group | 60 | 17.9 ± 5.2 | 26.0 |

Significance represented as *$P < 0.01$ compared with control group; ##$P < 0.01$ compared with curcumin group.

Compared to control group, Zn(II)-curcumin SDs markedly inhibited S180 sarcoma, and extended life span of mice with Ehrlich ascites tumor and HepA ($P<0.05$). Zn(II)-curcumin SDs had better anti-tumor effect than curcumin SDs ($P<0.01$).

Experiment Example 16

Protective Effects Against Carbon Tetrachloride-Induced Hepatic Injury in Rats

Reagents
Zn(II)-curcumin SDs (Zn(II)-curcumin and PVP in a ratio of 1:6, w/w), and curcumin SDs (1:6, w/w) were prepared with the same method of Mode 2 and were provided by Laboratory of Traditional Chinese Medicine and Marine Drugs, School of Life Sciences, Sun Yat-sen University, China. Polyvinylpyrrolidone K30 (PVP), was subpackaging of imported adjuvants provided by Guangzhou Chemical Agent, China. The reagents were dissolved in water for oral administration when used.

Animals
SD rats were provided by Guangdong Medical Laboratory Animal Center, China.
Forty healthy male SD rats (230±25 g) were randomly divided into 4 groups (n=10), namely normal group, control group, curcumin group and Zn(II)-curcumin group. Rats of normal and control group received equal amount of PVP solution, while curcumin and Zn(II)-curcumin group received SDs containing curcumin or Zn(II)-curcumin 60 mg/Kg body weight. Rats of normal group received arachisoil 5 ml/kg by peritoneal injection, while rats of other groups received 5 ml/Kg arachisoil (containing 25% $CCl_4$) for 10 successive days. At the $11^{th}$ day, all animals were fasted but with free access to water for 24 h. Blood was collected 1 h after oral administration and was centrifuged at 3000 rpm for 10 min. Content of alanine aminotransferase (ALT), aspartate aminotransferase (AST) and Albumin (Alb) in serum was determined.

Compared to control groups, Zn(II)-curcumin SDs exhibited protective effects against hepatic injury, by reducing the content of ALT and AST in serum and increasing the level of Alb in serum ($p<0.001$). Zn(II)-curcumin SDs showed better effects than curcumin SDs ($p<0.01$).

TABLE 19

Influence on ALT, AST and Alb in serum of rats (mean ± SD, n = 10)

| Group | Dose mg/kg | ALT (U/L) | AST (U/L) | Alb (g/L) |
|---|---|---|---|---|
| Normal | — | 38.44 ± 9.36*** | 145.63 ± 15.25*** | 51.25 ± 4.92*** |
| Control | — | 214.77 ± 19.47 | 253.27 ± 26.41 | 32.67 ± 5.12 |
| Zn(II)-curcumin | 60 | 94.52 ± 25.29****## | 172.30 ± 21.80****## | 42.15 ± 4.22****## |
| Curcumin | 60 | 129.82 ± 28.26*** | 195.62 ± 27.92** | 36.60 ± 4.38*** |

Significance represented as ***$P < 0.001$ compared to control group; ##$P < 0.01$ compared to curcumin group.

Experiment Example 17

Effect on the Duration of Immobility in the Forced Swimming Test

Reagents
Zn(II)-curcumin SDs (Zn(II)-curcumin and PVP in a ratio of 1:8, w/w), curcumin SDs (curcumin and PVP in a ratio of 1:8, w/w) were prepared by the same methods of Mode 2. They were provided by Laboratory of Traditional Chinese Medicine and Marine Drugs, Department of Biochemistry, School of Life Sciences, Sun Yat-Sen University, China. Polyvinylpyrrolidone PVP k30 (PVP), was subpackaging of imported adjuvants provided by Guangzhou Chemical Agent, China. Samples were dissolved in water when used and each group were treated with oral administration.

Animals

Kungming mice were provided by Guangdong Medical Laboratory Animal Centre, China.

Thirty male Kungming mice (18-25 g weight) were divided into three groups randomly, namely control group, curcumin SDs group and Zn(II)-curcumin SDs group. Every of them consisted of 10 mice. Mice of control group received equal amount of PVP solution, while curcumin group and Zn(II)-curcumin group received SDs containing curcumin or Zn(II)-curcumin 50 mg/Kg body weight once a day at the same time in the morning for 8 consecutive days. One hour after the last administration, mice were individually forced to swim for 6 min in glass cylinders (height: 30 cm, diameter: 18 cm), immersing 10 cm of water. Mice were observed for 4 min continuously after 2 min swimming. The duration of immobility or flotation was recorded during the last 4 min testing period and was compared between control group and drug administration group.

TABLE 20

Effect on the duration of immobility in the forced swimming test ($\bar{x} \pm$ S.D., n = 10)

| Group | Dose (mg/kg) | Duration of immobility (s) | Improvement percentage (%) |
|---|---|---|---|
| Control Group | — | 120.12 ± 28.43 | — |
| Zn(II)-curcumin group | 50 | 70.51 ± 20.24***# | 41.02 |
| Curcumin group | 50 | 92.43 ± 23.04* | 23.05 |

Significance represented as *$P < 0.01$, ***$P < 0.001$ compared with control group; #$P < 0.05$ compared with curcumin group.

Effect on the Duration of Tail Suspension in Mice

Thirty male mice (18-25 g weight) were divided into three groups randomly, namely control group, curcumin SDs group and Zn(II)-curcumin SDs group. Every group consisted of 10 mice. Mice of control group received equal amount of PVP solution, while curcumin group and Zn(II)-curcumin group received SDs containing curcumin or Zn(II)-curcumin 50 mg/Kg body weight once a day at the same time in the morning for 8 consecutive days. One hour after the last administration, mouse was suspended individually by its tail by placing a piece of adhesive tape 2 cm from the beginning of the tail and attaching the tape to the horizontal surface. Mouse head was 30 cm away from the table surface and the view of mouse was obstructed with wooden board. After 2 min of adjustment period, the duration of immobility was analyzed during a 6 min period of time.

TABLE 21

Effect on the duration of tail suspension in mice ($\bar{x} \pm$ S.D., n = 10)

| Group | Dose (mg/kg) | Duration of immobility (s) | Improvement percentage (%) |
|---|---|---|---|
| Control Group | — | 141.75 ± 31.24 | — |
| Zn(II)-curcumin | 50 | 74.26 ± 23.41***# | 47.61 |
| Curcumin | 50 | 105.92 ± 29.28* | 25.28 |

Significance represented as *$P < 0.01$, ***$P < 0.001$ compared with control group; #$P < 0.05$ compared with curcumin group.

Mice immobility in forced swimming test indicated mice behavioral despair. Compared with control group, curcumin SDs group and Zn(II)-curcumin SDs group significantly decreased the duration of immobility in forced swimming test ($p < 0.05$, $P < 0.001$). Both curcumin SDs group and Zn(II)-curcumin SDs group had anti-depression effect and Zn(II)-curcumin SDs group had a better effect curcumin SDs group ($p < 0.05$).

Mice immobility in tail suspension test indicated mice behavioral desperation. Compared with control group, curcumin SDs group and Zn(II)-curcumin SDs group obviously decreased the duration of immobility in tail suspension test ($p < 0.05$, $P < 0.001$). Both curcumin SDs group and Zn(II)-curcumin SDs group had anti-depression effect and Zn(II)-curcumin SDs group had a better effect than curcumin SDs ($p < 0.05$).

The invention claimed is:

1. A new Zn(II)-curcumin complex whose molecular structure showed in (I):

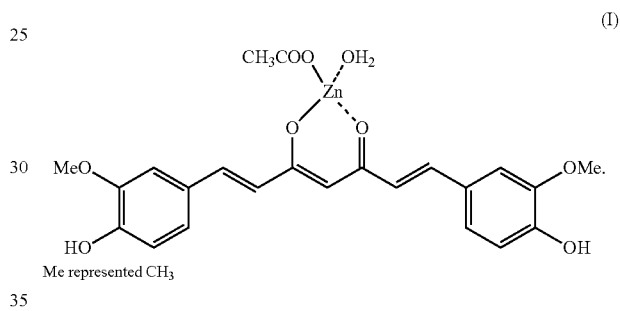

Me represented CH$_3$

2. A preparative method of the Zn(II)-curcumin complex of claim 1 comprising the steps of: dissolving zinc acetate and curcumin in organic solvents according to the molar ratio between 1:1-1:5; refluxing the zinc acetate and curcumin mixture for 3-5 h under a nitrogen atmosphere or in an oxygen-free environment at 45-70° C.; separating a resultant solid by filtration; washing said resultant solid 4-6 times at 5-15° C. in absolute ethanol to remove any unreacted curcumin and zinc acetate; subjecting said solid to vacuum dehydration.

3. The preparative method of claim 2 wherein said organic solvents are capable of dissolving zinc acetate.

4. A Zn(II)-curcumin solid dispersion having a Zn(II)-curcumin complex of claim 1 and polyvinylpyrrolidone (PVP) having a mass ratio between 1:10-1:28.

5. The preparative method of Zn(II)-curcumin solid dispersions of claim 3 further comprising: adding Zn(II)-curcumin and PVP proportionally to an absolute ethanol solution to produce a suspension by cryo-grinding under a nitrogen atmosphere; producing of Zn(II)-curcumin/PVP solid dispersions with a spray dryer.

6. The method of claim 3 wherein said solvent is ethanol or propyl alcohol.

* * * * *